United States Patent [19]

Ramwell et al.

[11] 3,932,656

[45] Jan. 13, 1976

[54] ARTICLE OF MANUFACTURE FOR INSTANT RELEASE OF ANTI-AGGREGATION AND NON-THROMBOGENIC AGENTS TO BIOLOGICAL MEDIA

[75] Inventors: Peter W. Ramwell, McLean, Va.; Hideo Shio, Kyoto, Japan; Jane E. Shaw, Atherton, Calif.

[73] Assignee: ALZA Corporation, Palo Alto, Calif.

[22] Filed: Dec. 20, 1973

[21] Appl. No.: 426,444

Related U.S. Application Data

[63] Continuation-in-part of Ser. No. 71,255, Sept. 10, 1970, abandoned.

[52] U.S. Cl. .................. 424/16; 424/183; 424/281; 424/305; 424/317; 424/319
[51] Int. Cl.² .................. A61K 9/00; A61K 31/19; A61K 31/195; A61K 31/725
[58] Field of Search ............ 424/16, 318, 317, 305, 424/183, 281, 319

[56] References Cited
UNITED STATES PATENTS

| | | | |
|---|---|---|---|
| 3,453,194 | 7/1969 | Bennett et al. | 424/183 |
| 3,475,358 | 10/1969 | Bixler et al. | 424/183 |
| 3,549,409 | 12/1970 | Dyck | 424/183 |
| 3,634,123 | 1/1972 | Eriksson | 424/183 |
| 3,673,612 | 7/1972 | Merrill et al. | 424/183 |
| 3,759,788 | 9/1973 | Gajewski et al. | 424/198 |

OTHER PUBLICATIONS

Emmons – Brit. Med. J., 2, 20 May 1967, pp. 468–472.

*Primary Examiner*—Sam Rosen
*Attorney, Agent, or Firm*—Paul L. Sabatine; Edward L. Mandell

[57] ABSTRACT

Polymeric materials having at least one exposed surface rendered as a release means for platelet aggregation inhibiting agent by serving as a reservoir for release of aggregation inhibiting prostaglandin. The polymeric surface can also be both platelet aggregation agent releasing and non-thrombogenic agent releasing by having together on the polymeric surface an aggregation inhibiting prostaglandin and an anti-coagulant which are easily released from the surface when in close contact with the blood, plasma or platelets.

11 Claims, No Drawings

ARTICLE OF MANUFACTURE FOR INSTANT RELEASE OF ANTI-AGGREGATION AND NON-THROMBOGENIC AGENTS TO BIOLOGICAL MEDIA

CROSS REFERENCE TO RELATED APPLICATION

This application is a continuation-in-part of our copending U.S. Pat. application Ser. No. 71,255, filed on Sept. 10, 1970, now abandoned which application is assigned to the same assignee of this application.

BACKGROUND OF THE INVENTION

This invention relates to an article of manufacture comprising polymeric materials having on its surface and coated therewith a platelet anti-aggregation compound alone, or in combination with other anti-aggregation agents and anti-thrombogenic substances, that are easily released therefrom. More particularly, the invention pertains to polymers having a platelet anti-aggregation prostaglandin incorporated into and coated onto the polymer surfaces and to polymeric materials having a prostaglandin and other anti-aggregation and anti-thrombogenic materials incorporated and coated onto the polymer surface as a means for adding these to passing, contacting biological media.

The rapid advances in polymer research with its genesis of polymeric materials has been accompanied with an accelerated use of the polymeric materials for medical engineering, for medical drug delivery devices, and medical applications for the management of health. These uses of polymeric materials for medical engineering include cardiac pacemakers, heart valve prosthesis, artificial kidneys, and heart-lung machines. The use of polymeric materials for the management of health include blood and platelet collecting systems, transfusions, the preparation of blood components for use in blood loss and the like. The use of polymeric materials as drug delivery devices include the use of these materials as solution diffusion materials for the release of a drug from a drug reservoir. Yet, in all these uses, the art has heretobefore encountered serious problems that defeated the desired aim. For example, even though there are a wide number of available polymers, such as homopolymers, copolymers, terpolymers, cross-linked polymers, thermoplastic and thermosetting polymers, and the like, the adverse effects produced by these polymeric substances has posed very serious obstacles to the successful employment of these polymers for the above mentioned purpose. These problems included the initiation of blood coagulation and the aggregation of platelets. This coagulation or thrombogenic property of polymers and the aggregation or clumping of platelets by polymers, has led the prior art, especially when it used the polymers for the manufacture of medical devices, to attempts to avoid the unfavorable disposition of these polymers. These attempts often focused on the surface electrical charge of a polymer and efforts were made to correlate the polymeric charge with the naturally occurring potential on the polymer interface but the correlations were seemingly unsuccessful. Other efforts in the art were predicated on the regulation of the flowing blood through polymeric systems to control excessive turbulence which may lead to blood coagulation and platelet aggregation and on the chemical alteration of the polymeric surface by coating the polymer with an anticoagulant to prevent thrombic formations. It is self apparent that these latter two efforts have not met with acceptable success because of the difficulties associated with controlling the flow of liquids through conduits, the lack of a smooth internal surface, the difficulties in coating the porous lattice of a predetermined polymer and the like. Also, while the prior art has attempted to render the polymeric material non-thrombogenic, it has not seriously attempted to render the polymeric material either platelet aggregation inhibiting alone or both simultaneously aggregation inhibiting and non-thrombogenic. Other thoughts pertaining to anti-thrombogenic effects for medical devices involved the use of polyelectrolyte complex polymers having excess polycation as retardants; however, these thoughts have not offered a practical answer to the immediate problem of the present invention as presented hereinafter.

In all of the just described attempts and uses, the prior art sought to permanently bond or unite the active agent to a polymer. This too had its shortcomings, for in many instances it is both highly desirable and needed to quickly add the agent to blood or platelets. For example, in the processing of platelets starting with the collection of blood, it is now necessary to add platelet protecting agents to blood after it arrives in a collection bag. That is, during the processing, the platelets flowed unprotected through the collection apparatus. It is well known that platelets are very sensitive and rendered non-viable during such unprotected processing. Additionally, the prior art never conceived or attempted to produce any articles of manufacture that easily released an active agent to a platelet media. That is, the prior art never made an article of manufacture where an active platelet protecting agent is imbibed and surface coated onto a polymer for easy release of the agent on mere contact to the flow of a passing liquid. It will be appreciated by those versed in the art to which the invention pertains that a critical need exists for an article that easily releases an active agent to protect platelets for retaining their properties for use in health and disease.

OBJECTS OF THE INVENTION

Accordingly, it is a primary purpose of this invention to provide an article of manufacture that easily releases a platelet protecting agent on contact by a platelet.

Yet another object of the invention is to provide a biologically acceptable synthetic polymer having incorporated into its surface and coated thereon a platelet aggregation inhibiting prostaglandin that is easily released to blood, plasma and platelets.

Still another purpose of the invention is to provide a synthetic non-ionic polymeric surface member having releasably, intimatly deposited thereon but chemically and ionically unbonded thereto, a platelet inhibiting prostaglandin adapted to be loosed from said surface member in response to the flow of liquids.

Still a further object of the invention is to provide a polymeric surface having imbibed and coated thereon, but covalently unbonded thereto, a platelet protecting prostaglandin that is easily released to a contact passing media needing said prostaglandin.

Yet still a further purpose of the invention is to incorporate anti-aggregation agents into polymeric surfaces to act as a reservoir of the agents that are releasable in contact with blood to provide an anti-aggregation agent to the blood.

It is a further object of the instant invention to provide a polymeric substance which has both a platelet aggregation inhibiting agent and a non-thrombogenic agent that is instantaneously released to a contacting medium needing such agents.

Still a further purpose of the invention is to provide a simple and efficient means for treating polymeric material whereby the material is rendered anti-aggregation or jointly anti-aggregation and non-thrombogenic for instant transfer to a passing agent receptor.

It is additionally an immediate object of this invention to make available to the art a homogenous polymeric material that possesses platelet aggregation inhibiting agents thereon wherein the agent is a prostaglandin in its unchanged physicochemical form.

Yet still a further object of the invention is to imbibe certain anti-aggregation agents into polymeric surfaces employed for release in prosthetic and transfusion purposes.

Yet still a further object of the invention is to provide predetermined shaped articles having non-thrombogenic and anti-aggregation surfaces of releasable non-thrombogenic and anti-aggregation agents that are released without intervening physical and chemical methods.

Other objects, features and advantages of the invention will become apparent to those versed in the art from the following description, examples and the appended claims.

SUMMARY OF THE INVENTION

This invention concerns an article of manufacture comprised of a synthetic, polymer surface rendered instant releasable to essential platelet aggregation inhibiting prostaglandins by treating the polymer surface such that the prostaglandin is released on contact to a contacting agent. The polymer surface can also be rendered releasable for aggregation inhibiting agents, by intimately contacting the polymer surface with a composition of matter comprising an aggregation inhibiting prostaglandin and if preferred, at least one or more additional platelet aggregation inhibiting agents that are released in response to the flow of liquid. The invention also concerns polymer surfaces that act as a reservoir for both non-thrombogenic and anti-aggregation agents that are discharged from the polymeric reservoir by contacting the polymeric surface. The polymeric treated surfaces also act as a reservoir for an aggregation inhibiting prostaglandin alone, or with a composition containing a prostaglandin and an anti-coagulant, that is made available to the blood, platelets and the like when they come into contact with a treated polymeric surface.

DESCRIPTION OF THE INVENTION

The above objects, features and advantages of the invention are unexpectedly achieved as a result of the discovery that polymers can be rendered releasable to platelet aggregation inhibiting agents, especially prostaglandins, by intimately contacting the polymeric surface with a prostaglandin that essentially inhibits platelet aggregation or clumping on its release from the polymer surface. The expressions "aggregation inhibiting" and "anti-aggregation" are used herein as equivalents to mean essentially the prevention or inhibition of clumping or aggregation of the platelets. From henceforth in this specification only the expression "aggregation inhibiting" will be used in the disclosure. The polymeric surface can be rendered releasable to aggregation inhibiting prostaglandins by employing the prostaglandin alone, or in homogenous combination with other aggregation inhibiting releasable agents. Also, the invention contemplates that the polymeric surface can be rendered simultaneously releasable to both aggregation inhibiting agents and anti-thrombogenic agents by treating the polymeric surface with an aggregation inhibiting prostaglandin and an anti-thrombogenic agent which retain their physical and chemical integrity and are release unmodified and unchanged to a contacting passing liquid or the like.

The polymeric materials suitable for the purpose of the present invention, that is, as a releasable carrier, are the polymeric materials physiologically acceptable for contacting tissues, blood and organs and the materials generally exhibit properties such as non-toxicity, flexibility, non-irritability, chemical stability, ease of fabrication into articles such as implants, valves, joints and the like. More importantly, the polymeric materials are those that can be imbibed and coated on the surface with a prostaglandin that is loosed or released from the surface in response to the flow of a liquid. Exemplary of polymeric materials include polyolefins such as polyethylene and polypropylene, polyvinylchloride, polytetrafluoroethylene, polychlorotrifluoroethylene, polymethylmethacrylate, polyacrylonitrile, polyethylene terephthalate, butadiene-vinylpyridine copolymer, polyamides, nylon and the like. These commercially available polymers can be obtained in a variety of shapes and forms such as bags, pouches, tubing, sheets, rods, blocks, powder and the like from which the desired predetermined part can be made or used for the intended purpose.

The primary platelet aggregation inhibiting agent employed according to the spirit of this invention for imbibing and coating onto polymeric exposed surfaces are the naturally occurring and synthesized prostaglandin compounds possessing platelet aggregation inhibiting properties. The prostaglandins possessing this biological property include the structurally active analogues, homologues and steriosomers. These compounds are characterized as having a carbon skeleton that is a derivative of prostanoic acid, the parent non-nitrogenous $C_{20}$ acid of the biologically active prostaglandins. The formula of prostanoic acid and the numbering system are as depicted in FIG. 1.

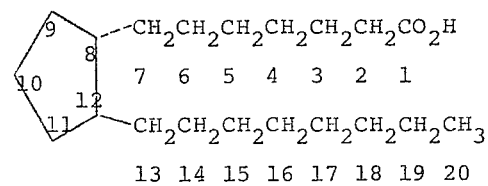

Figure 1

Thus, in view of this structure, prostaglandins are usually considered as unsaturated $C_{20}$ fatty acids with five of the carbon atoms forming a cyclopentane ring which can be construed as a nucleus to which two side chains are attached in the vicinal position. The stereochemistry of the chain substituents on the 5-membered ring has been designated as alpha ($\alpha$) or beta ($\beta$); and the α-substituents are oriented on the same side of the ring as the carboxy side chain attached to the C-8 atom and the β-substituents are oriented in the opposite sense as the alkyl C-13 to C-20 side chain. In the above formula, and in other formulas used herein, a dotted line represents a valency bond in the α-configuration, a solid line a valency bond in the β-configuration, and a wavy bond indicates either α or β configuration. For further classification, the prostaglandins are described as E, F, A and B respectively, depending on the substituents and valency of the 5-membered ring. The E-type prostaglandins, FIG. 2 and its diastereomers, have an 11-hydroxy (OH) and a 9-keto (C=O) group in the 5-membered ring.

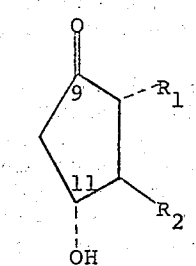

Figure 2

In the F-type prostaglandins, represented by FIG. 3, the 9-keto is reduced to a hydroxyl group.

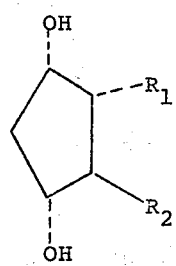

Figure 3

The F-type prostaglandins also include the diastereomers of the depicted structure. The nucleus of the A-type prostaglandins, FIG. 4 and its diastereomers, retains the 9-keto group but it has a double bond at the 10:11 position of the nucleus, thusly.

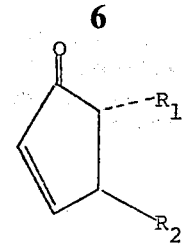

Figure 4

The nucleus of the B-type prostaglandins retains the characteristic 9-keto group with the further identifying feature of a 8:12 double bond as set forth in FIG. 5

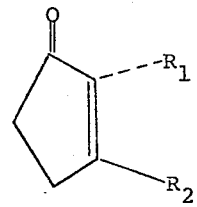

Figure 5

Among the naturally occurring prostaglandin compounds, two side chains designated as $R_1$ and $R_2$ have been described in the literature. One side chain, the chain identified as $R_1$, contains a terminal carboxylic acid group (COOH) and it may also contain a double bond, while the other side chain, $R_2$, contains a hydroxyl functional group together with one or more double bonds. These side chains are present in the prostaglandins in three combinations and are designated at 1, 2 and 3 respectively, so that the prostaglandins are designated as $E_1$, $E_2$, $E_3$, $F_1$, $F_2$, etc. All the primary prostaglandins contain a 13:14 trans oriented double bond. If the valencies of the $C_{13}$ and $C_{14}$ atoms are satisfied with a hydrogen or the like, the prostaglandin nomenclature omits the trans description in naming the structure of the prostaglandin. The $E_1$ and $F_1$ compounds contain only this one double bond; while the $E_2$ and $F_2$ molecules have an additional 5:6 double bond. The following box diagram further elucidates the chemical structure of the prostaglandin side chains.

| Prostaglandins | $R_1$ | $R_2$ |
| --- | --- | --- |
| $E_1$, $F_1$, $A_1$, $B_1$ | —(CH$_2$)$_6$COOH | —CH:CHCH(OH)(CH$_2$)$_4$CH$_3$ |
| $E_2$, $F_2$, $A_2$, $B_2$ | —CH$_2$CH:CH(CH$_2$)$_3$COOH | —CH:CHCH(OH)(CH$_2$)$_4$CH$_3$ |
| $E_3$, $F_3$, $A_3$, $B_3$ | —CH$_2$CH:CH(CH$_2$)$_3$COOH | —CH:CHCH(OH)CH$_2$CH:CHCH$_2$CH$_3$ |

The prostaglandins based upon the above described chemical structure that are operable according to the mode and the manner of the present invention are the physiologically acceptable platelet aggregation inhibiting E-type prostaglandins and the E-type-like prostaglandin-like compounds that can be represented by the following formula designated as FIG. 6, and the diastereomers thereof represented by the formulas designated as FIG. 7 and FIG. 8:

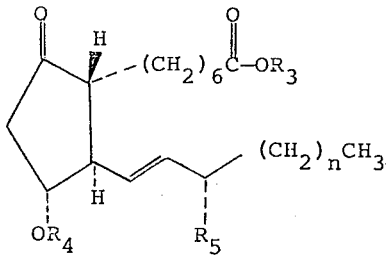

Figure 6

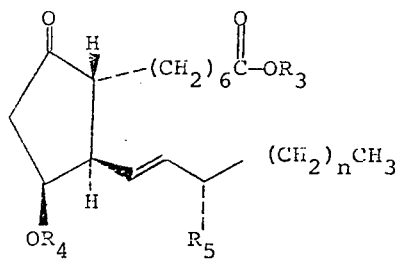

Figure 7

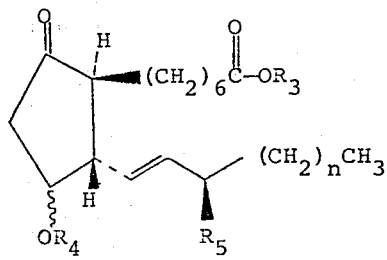

Figure 8 and wherein in formulas of FIGS. 6, 7 and 8, $R_3$ is hydrogen or a lower alkyl group of 1 to 8 carbon atoms inclusive; $R_4$ is a member selected from the group consisting of hydrogen, lower alkyl and the acyl group of a hydrocarbon carboxylic acid of 2 to 18 carbon atoms, $R_5$ is a hydroxyl group, n is a positive whole integer of 3 to 5 inclusive, and $OR_4$ and $R_5$ may have an $\alpha$ or $\beta$ configuration, the broken line indicating $\alpha$ configuration, the solid line $\beta$ configuration, and a wavy line either an $\alpha$ or $\beta$. Exemplary of lower alkyl groups suitable for the purpose of the invention are the straight or branched chain hydrocarbon group containing 1 to 8 carbon atoms inclusive such as methyl, ethyl, propyl, isopropyl, n-butyl, tertbutyl, pentyl, neopentyl, n-hexyl, isohexyl, n-octyl and the like. Representative of acyl moities are formyl acetyl, propionyl, butyryl, valeryl, caproyl, octanoyl, lauroyl, palmitoyl, stearoyl, oleoyl and the like.

The pharmaceutically acceptable, non-toxic salts of the prostaglandins can also be used including the non-toxic alkali metal and alkaline earth metal bases such as sodium, potassium, calcium, lithium and copper, and magnesium hydroxides and carbonates and the ammonium salts and substituted ammonium salts, for example, the non-toxic salts of trialkylamines such as triethylamine, trimethylamine, triisopropylamine, procaine, epinephrine, dibenzylamine, triethanolamine, N-benzyl-betaphenylethylamine, ethyldimethylamine, benzylamine, N-(lower) alkylpiperdine, N-ethylpiperidine, 2-methylpiperidine, and other acceptable amines. The presently preferred structure for aggregation inhibiting effects as set forth above is of the prostaglandin E-type configuration. The aggregation inhibiting properties for the prostaglandins are believed due to the presence of the C=O group of the carboxyl group or the C=O of the esterified carboxyl group, the presence of the hydroxyl group at the C-15 position of the $R_2$ side chain and the keto group at the C-9 position of the cyclopentane nucleus.

The active prostaglandins used according to the spirit of the invention may be successfully employed alone, in combination with one or more prostaglandins or in homogeneous, intimate compositions comprising at least one prostaglandin and other known physiologically acceptable platelet aggregation inhibiting agents. For example, the prostaglandin $E_1$ as set forth in FIG. 9 and having the following structure,

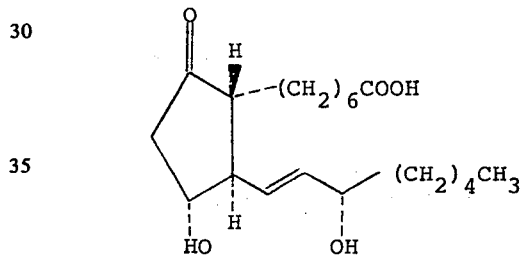

Figure 9 can be used alone or it can be used mixed in composition with its lower alkyl ester as shown in FIG. 10,

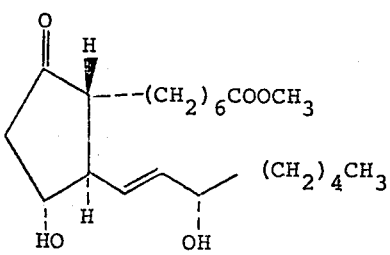

Figure 10 or it can be used in combination with its homologues, for example, FIG. 11,

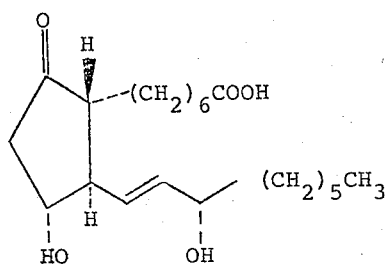

Figure 11 or with mixtures thereof as taught by the above formulae. The active prostaglandins can also be intimately compounded with other physiologically acceptable aggregation inhibiting agents into a homogeneous composition of matter for the purpose of this invention. Other compounds that act as platelet aggregation inhibiting agents are acetylsalicylic acid, methyl benzoyl ecgonine, cetyl-pyridinium bromide, toluidine blue, purine riboside, 2-oxy-6-amino purine riboside, agmatine cysteine and the like.

The aggregation inhibiting agents can be applied to the prepared receptive polymeric surface for incorporation therein and coating thereon in any amounts. Usually, a solution containing 1 to 20 percent by weight is brought into immediate contact with the polymer surface to produce the desired effects. Generally, about 0.1 microgram to 200 micrograms of biologically active platelet aggregation inhibiting agent for each centimeter square of exposed polymer surface is acceptable for achieving the desired release results; however, larger concentrations can be employed if so desired.

The prostaglandins can also be mixed into a composition with anti-thrombogenic materials and applied to polymeric surfaces to simultaneously render the polymeric surface releasable to both anti-thrombogenic and aggregation inhibiting agents. Suitable anti-thrombogenic agents include sulfated polysaccharides such as heparin, coumarin type compounds such as dicoumarol, indandions like warfarin, ethylenedeamine tetra-acetic acid and the like. The amount of anti-thrombogenic agent employed for release will also be about 1 to 20 weight percent and it will usually be admixed with the anti-aggregation agent in a common carrier. Usually, about 0.1 microgram to 200 micrograms of biologically acceptable anti-thrombogenic material is incorporated into each centimeter square of polymer surface for producing the intended releasable results. The above anti-thrombogenic material and aggregation inhibiting materials may be applied to receptive polymeric surfaces wherein the polymeric surfaces are rendered receptive by the surface organic treatment process and the plasticizer process. Both of these processes produce a surface that releases the agent imbibed and coated thereon. The two procedures are described immediately below. In the releasable organic process, the first step is to intimately contact the polymer's surface with a commercially available organic solvent or carrier for the active agent for a predetermined exposure time to effectively permit the active agent, such as the prostaglandin to coat the surface of the polymer and also to imbibe into the polymer surface and into the polymeric body just beneath the outer exposed polymer surface. The releasable plasticizer process generally involves the first process step of heating the polymer in a vehicle containing plasticizer and the active agent or heating the polymer in a liquid plasticizer containing the active agent to effectively permit the plasticizer containing the active agent to be lightly imbibed and to distribute itself into the surface of the polymer.

The anti-aggregation agent can be applied using these two processes singly or in combination with anti-thrombogenic agents by art known techniques, either manually or mechanically performed, such as spatula spreading, roller coating, cold dip, squeeze, brush, hot dip, doctor blade, soaking, continual rinse, or by any other like means. Finally, any excess solvent or plasticizer is removed by evaporation at room temperature, vacuum stripping, by drying in a gaseous stream of an inert atmosphere such as nitrogen, argon or the like. In the above fabrication techniques, the active agent is generally contacted or applied to the polymeric surface for about 10 minutes to about 1440 minutes for effectively imparting releasability of the platelet anti-aggregation agent to the polymeric surface, singly, or coupled with a releasable non-toxic anti-thrombogenic agent.

Exemplary of plasticizers suitable for employment for the present purpose are the commercially available plasticizers such as diethyl adipate, di-isobutyl adipate, di-n-hexyl adipate, di-isoctyl adipate, di-n-hexyl azelate, di-2-ethylhexylazelate, ethylene glycol dibenzoate, acetyl tri-n-butyl citrate, epoxidized soy bean oil, glycerol monoacetate, diethylene glycol dipelargonate, propylene glycol dilaurate, isooctyl palmitate, triphenyl phosphate and the like.

Representative of solvent vehicles acceptable for the purpose of the present invention include the solvents such as tetrahydrofuran, chloroform, acetone, methylene chloride, ethylene chloride, dioxane, isobutyl ketone, methyl isobutyl ketone, dimethylether, diethylether, alkanols such as methanol, butanol, n-amyl alcohol, 2-ethylhexyl alcohol, ethylene glycol, ethanol, isopropanol, hexanol, butanol, pentanol and solvents such as benzene, carbon tetrachloride, cycloalkanes such as cyclopentane, 1,2-dimethylcyclopentane, cyclooctane, isopropylcyclohexane, cyclohexane, methylcyclohexane, alkanes such as 3-methylpentane, n-hexane, h-heptane, lower fatty acid esters like amyl acetate, ethylacetate and the like. The solvent used must be able to release the agent to the polymer while simultaneously maintaining the physical and chemical integrity of the prostaglandin. Those solvents that have adverse effects on prostaglandins are not suitable for the purpose of this invention.

The following examples will further serve to illustrate the invention and these examples are not to be construed as limiting as other embodiments will become apparent to those versed in the art from a reading of the present disclosure and the accompanying claims.

EXAMPLE 1

A 15 centimeter section of commercially available polyethylene catheter tubing with an approximate internal diameter of 5 millimeters and an outside diameter of about 15 millimeters is first immersed in a bath of 2 molar ethyl acetate freshly prepared, for about 7 to 8 minutes to remove any unwanted foreign matter from the polyethylene surface. Next, the tubing is removed from the bath and it is rinsed with distilled water. Then, the tubing is reimmersed in a freshly prepared 10% ethylacetate solution of 11α,15α-dihydroxy-9-oxo-13-trans-prostenoic acid and it is permitted to soak therein for 7 to 9 hours. This process with the prostenoic acid renders the polymeric surface platelet aggregation inhibiting agent releasable for the intended purpose.

EXAMPLE 2

A solution of 350 mg of 11α,15(S)-dihydroxy-9-oxo-13-transprostenoic acid in 100 ml of dry acetone is prepared and maintained at room temperature in a 500 ml round bottom flask. Next, a section of medical grade plasticized poly(vinyl chloride) tubing about 40 cm long and having an internal diameter of 0.5 cm and an outside diameter of 1 cm is immersed in the acetone and allowed to remain in contact with the solution for 15 minutes. The tubing is then removed and it is allowed to air-dry for 24 hours at room temperature to remove the solvent from the surface and from the body of the tubing. Next, the tubing is conditioned in a circulating nitrogen oven at 45°C to 50°C for 72 hours to remove the last traces of solvent. The tubing now has an exterior layer of 11α,15(S)-dihydroxy-9-oxo-13-trans-prostenoic acid as a result of its having been imbibed into the outer surface layers of the tubing, for instant release in response to the flow of liquid therethrough.

EXAMPLE 3

A solution of 150 mg of 11α,15(S)-dihydroxy-9-oxo-13-trans-8-iso-prostenoic in 50 ml of dioctyl adipate is freshly prepared and warmed to about 50°C. Next, a section of medical grade plasticized poly(vinyl chloride) tubing is immersed into the adipate solution and the tubing is allowed to remain immersed for 12 hours. After 12 hours immersion, the tubing is removed and allowed to condition in a mixed nitrogen-air environment at 50°C for 48 hours. The dioctyl adipate which has been imbibed will distribute itself uniformly through the plasticized medical grade poly(vinyl chloride) tubing while the prostenoic acid imbibed along with the dioctyl adipate, will tend to remain concentrated in the surface layers of the tubing to serve as a reservoir for future release of the prostaglandin.

EXAMPLE 4

To 500 ml of reagent grade chloroform at 45°C is added 150 mg of 11α,15(S)-dihydroxy-9-oxo-13-trans-prostenoic acid, prostaglandin $PGE_1$, with stirring to effect complete solution. Next, 50 grams of a copolymer of 57 parts by weight of propylene and 43 parts by weight of vinyl propionate is added and stirring is maintained continuously to effect solution. This solution is now used as a dip coating to deposit prostaglandinrich layers of propylene/vinyl propionate copolymer on variously shaped medical objects which are composed of copolymers of propylene and vinyl propionate whose composition may include a range of compositions containing from about 40 per cent to 48 per cent vinyl propionate. After dipping the shaped forms of propylene/vinyl propionate copolymers in the above-described solutions, the objects are then dried free of solvent chloroform by drying in a circulating air oven at 50°C for 16 hours. Additional dip coats may be applied by repeating the above operation.

EXAMPLE 5

The procedure as set forth in Example 4 is repeated in this example and all processing conditions are as described with the prostenoic acid, 11α,15(S)-dihydroxy-9-oxo-13-trans-ω-homo-prostenoic, prostaglandin ω-homo-$PGE_1$, substituted for the prostenoic acid of Example 4. The prostaglandins of this example are adapted to be loosed from the surface member in response to the flow of liquids.

EXAMPLE 6

A prostaglandin solution of 50 mg of 11α,15(S)-dihydroxy-9-oxo-13-trans-prostenoic acid in 100 ml of reagent grade ethyl acetate is prepared at 25°C with stirring. An artificial heart valve poppet constructed from nylon is allowed to steep in this solution for 4 hours at room temperature. After removal from the prostaglandin solution, the heart valve poppet is allowed to dry free of ethyl acetate by exposure for 4 days at 60°C in a vacuum oven at a pressure of 5 mm of mercury. The heart valve poppet will then have a deposited residue of prostaglandin in the first 0.040 inch of the exposed surface. The prostaglandin is released on contact with blood to protect the platelets.

EXAMPLE 7

A square section of polypropylene of about 50 cm by 50 cm by 0.5 cm is solvent coated in a methanol solution containing 10% of 3-(α-acetonybenzyl)-4-hydroxycoumarin and 10% of 11α, 15α-dihydroxy-9-oxo-13-trans-prostenoic acid for 18 to 24 hours, at room temperature. Next, the excess solvent is stripped off and the polymeric surface is dried in a nitrogen environment. The prostaglandin is deposited onto and in the outer surfaces of the polymer and it acts as a surface reservoir of the prostaglandins that are released or loosed from the reservoir to the flow of blood, platelets or a contacting biological surface in need of platelet protecting agents. The article made possible the preservation of viable platelets for use in the management of health and disease.

Active agents were bonded to polymer by procedures available to the art such as the graphite process, the haloalkylation process, the radiation process, the ionic resin process and the like, which processes are not suitable for the purpose of this invention. That is, these processes firmly fixed their agent to the polymer and preclude any releasability therefrom. For example, in prior art U.S. Pat. No. 3,598,858, there is disclosed adsorption of prostaglandins onto a resin. The adsorption onto the resin is effected by ionizing the prostaglandin acid. The ionic form of the prostaglandin interacts strongly with the positively charged sites on the resin and it is ionically bonded to the resin. To remove the ionic form of the prostaglandin it is necessary to adjust the pH to remove the prostaglandin from the resin, as they cannot be removed by contact. In U.S. Pat. No. 3,453,194 there is disclosed non-thrombogenic heparin covalently bonded to silicone. The covalent bond is essentially nonrupturable and it is non-releasable to the agent. This patent also grafts heparin to silicone by the use of a high energy accelerator to form a free radical which essentially covalently bonded heparin to the polymer. The products formed are nonreleasable and the structure of the bonded compound is altered through the formation of these bonds.

In French Pat. No. 1,459,646 there is employed either a cationic or anionic surface active agent to form either a cationic or an anionic complex to permanently bond the protective compound through the complex to the polymer. This procedure cannot give the claimed results. In *British Medical Journal*, pages 468 to 472, published May 1967, the author disclosed the use of prostaglandins to prevent platelet glass adhesiveness. This reference too leads away from the present invention, as glass is impermeable and cannot be used for imbibing and coating with the prostaglandin. That is, glass is dense and hard as there is no molecular movement which structural features preclude imbibing and coating. In the glass adhesiveness the presence of prostaglandins serves to prevent platelet-to-glass contact, and glass cannot be used as a drug carrier release rate reservoir for prostaglandins. In German Pat. No. 1,943,492 there is disclosed diffusion of prostaglandins from within vulcanized polysiloxane. Diffusional release for the system is slow and it is not adapted for instant surface release. In U.S. Pat. No. 3,549,409 there is disclosed non-thrombogenic plastic produced by a metal ion bondality to permeanently fix heparin to polymers. This process requires the use of polyvalent metals to bond highly negatively charged heparin, and ammonium hydroxide which may be harmful to the prostaglandins. In U.S. Pat. No. 3,616,935 anti-thrombogenic surfaces are prepared by bonding the material through polyalkylenimine. This usually involves functional groups to form a non-releasable product. Accordingly, it can be seen from the above presentation, the prior art does not lend itself as a means for arriving at the present invention.

Having thus described the invention and various embodiments thereof that contribute to the art a novel and unobvious article of manufacture containing releasable prostaglandins that inhibit platelet aggregation and is useful for collecting, storing and transfusing platelets, for fabricating prosthetic parts, for laboratory platelet studies and the like, it is to be understood that the disclosure is not to be construed as limiting, as these embodiments and other variations will be obvious to those versed in the art from a reading of the present invention.

We claim:

1. A novel article of manufacture wherein said article consists essentially of a biologically acceptable synthetic polymer having imbibed into its outermost surface and coated thereon a platelet aggregation inhibiting amount of prostaglandin that is easily released when contacted with blood, plasma and platelets and wherein the prostaglandin is a compound selected from those of the formulae:

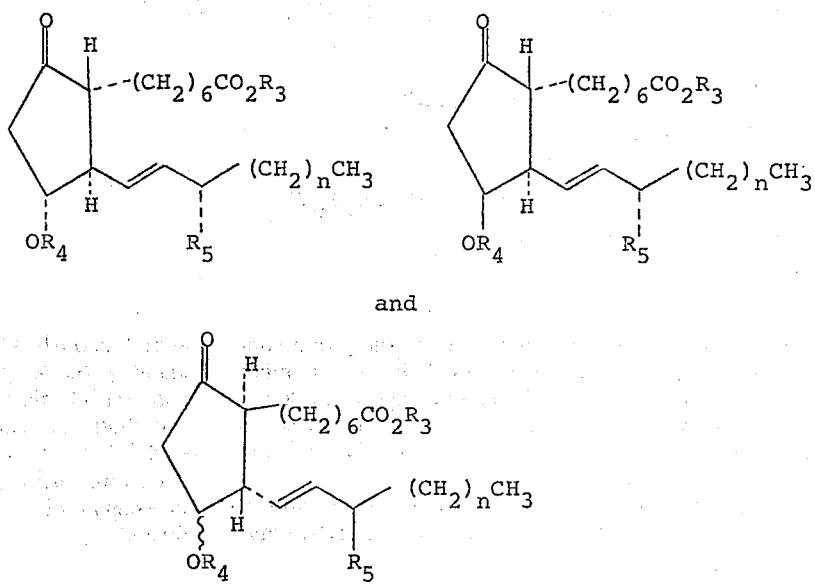

wherein $R_3$ is a member selected from the group consisting of hydrogen and lower alkyl, $R_4$ is a member selected from the group consisting of hydrogen, lower alkyl and an acyl group of 2 to 18 carbons, $R_5$ is hydroxy, $n$ is a whole integer of 3 to 5 inclusive, and the diastereomers thereof.

2. An article of manufacture according to claim 1 wherein the prostaglandin is 11α,15(S)-dihydroxy-9-oxo-13-trans-prostenoic acid.

3. An article of manufacture according to claim 1 wherein the prostaglandin is 11α,15(S)-dihydroxy-9-oxo-13-trans-8-isoprostenoic acid.

4. An article of manufacture according to claim 1 wherein the prostaglandin is 11α,15(S)-dihydroxy-9-oxo-13-trans-ω-homoprostenoic acid.

5. An article of manufacture according to claim 1 wherein the biologically acceptable synthetic polymer is shaped, silica-free and non-ionic, and wherein the prostaglandin is releasably, intimately physically deposited thereon, but chemically and ionically unbonded thereto, thus defining a prostaglandin reservoir responsive to the flow of liquid thereover.

6. An article of manufacture consisting essentially of a biologically acceptable synthetic polymer and wherein the polymer has at least one blood contacting surface rendered releasable to a non-thrombogenic agent and an anti-aggregation agent by having releasably incorporated into the polymeric surface and releasably coated thereon a coagulation inhibiting amount of a anti-thrombogenic agent and a platelet aggregation inhibiting amount of an anti-aggregation agent wherein the anti-thrombogenic agent is a member selected from the group consisting of heparin, coumarin, dicumarol and warfarin and wherein the anti-aggregation agent is a prostaglandin compound selected from those of the formulae:

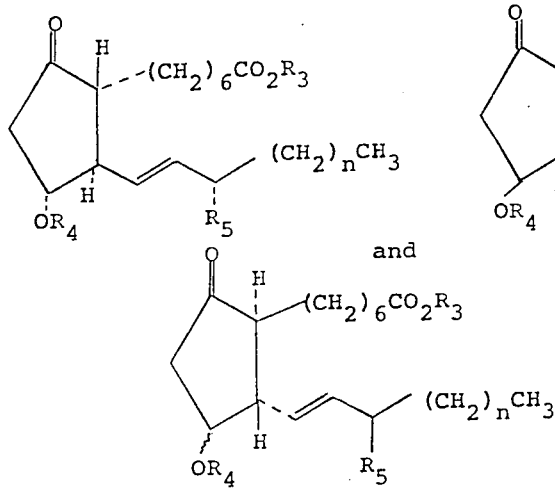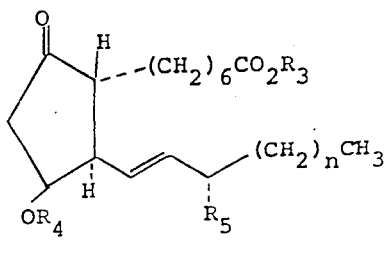

wherein $R_3$ is a member selected from the group consisting of hydrogen and lower alkyl, $R_4$ is a member selected from the group consisting of hydrogen, lower alkyl and an acyl group of 2 to 18 carbons, $R_5$ is hydroxy, $n$ is a whole integer of 3 to 5 inclusive, and the diastereomers thereof.

7. An article of manufacture according to claim 6 wherein the anti-aggregation agent is 11α,15(S)-dihydroxy-9-oxo-13-trans-prostenoic acid.

8. An article of manufacture according to claim 6 wherein the anti-aggregation agent is 11α,15(S)-dihydroxy-9-oxo-13-trans-8-iso-prostenoic acid.

9. An article of manufacture according to claim 6 wherein the anti-aggregation agent is 11α15(S)-dihydroxy-9-oxo-13-trans-ω-homo-prostenoic acid.

10. An article of manufacture according to claim 6 wherein the anti-thrombogenic agent is heparin.

11. A process for essentially protecting blood, plasma and platelets against the platelet aggregation effects of a plastic surface when the blood, plasma and platelets are in contact with the plastic surface and also for simultaneously adding a platelet aggregation inhibiting agent to blood, plasma and platelets when in contact with the plastic surface, wherein the process consists essentially of rendering the plastic surface free from said effects by first coating the plastic surface with at least one anti-aggregation prostaglandin wherein the prostaglandin is a compound selected from those of the formulae:

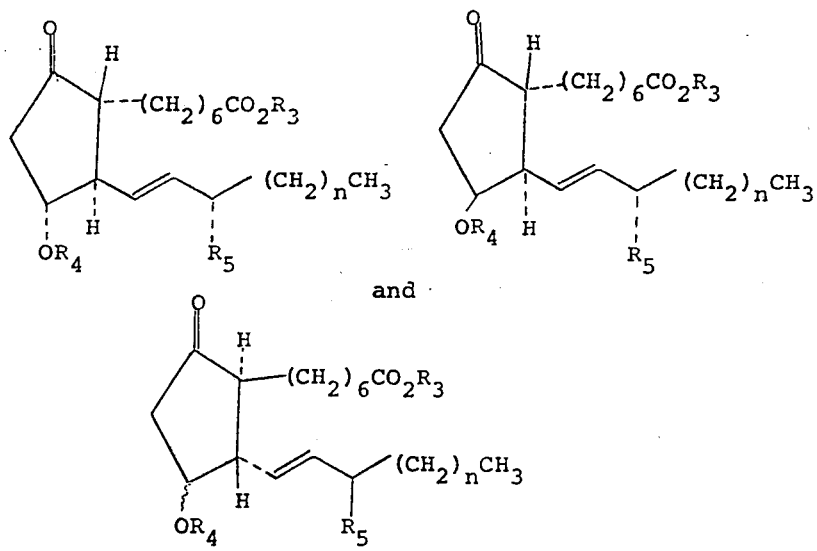

wherein $R_3$ is a member selected from the group consisting of hydrogen and lower alkyl, $R_4$ is a member selected from the group consisting of hydrogen, lower alkyl and an acyl group of 2 to 18 carbons, $R_5$ is a hydroxy, $n$ is a whole integer of 3 to 5 inclusive, and the diastereomers thereof, said prostaglandin being released from the coated surface in a platelet aggregation inhibiting amount to protect said blood, plasma and platelets against said platelet aggregation effects of the polymer upon contact therewith, while simultaneously adding the prostaglandin to the blood, plasma and platelets.

* * * * *